United States Patent [19]
Quattrocchi

[11] Patent Number: 5,978,466
[45] Date of Patent: Nov. 2, 1999

[54] METHOD AND SYSTEM FOR ANONYMOUSLY TESTING FOR A HUMAN MALADY

[75] Inventor: Richard A. Quattrocchi, Hoffman Estates, Ill.

[73] Assignee: Home Access Health Corporation, Hoffman Estates, Ill.

[21] Appl. No.: 08/942,903

[22] Filed: Oct. 2, 1997

Related U.S. Application Data

[62] Division of application No. 08/877,702, Jun. 16, 1997, which is a continuation of application No. 08/420,694, Apr. 12, 1995, abandoned, which is a continuation-in-part of application No. 08/146,307, Nov. 2, 1993, abandoned.

[51] Int. Cl.$^6$ ........................................ H04M 3/00
[52] U.S. Cl. ........................ 379/265; 379/67; 379/70; 379/196; 379/212; 379/309; 435/5; 435/7.92; 435/974; 436/530; 422/55; 422/56; 364/340; 364/400; 364/413.01; 364/413.07
[58] Field of Search ............................. 435/5, 7.92, 974; 436/530; 422/55, 56; 364/340, 400, 413.01, 413.07; 379/265, 67, 70, 196, 212, 309

[56] References Cited

U.S. PATENT DOCUMENTS

| | | |
|---|---|---|
| 3,272,319 | 9/1966 | Brewer . |
| 3,883,396 | 5/1975 | Thomas et al. . |
| 3,933,439 | 1/1976 | McDonald . |
| 4,122,947 | 10/1978 | Falls . |
| 4,240,547 | 12/1980 | Taylor . |
| 4,277,249 | 7/1981 | Broughton . |
| 4,522,302 | 6/1985 | Paikoff . |
| 4,777,964 | 10/1988 | Briggs . |
| 4,792,968 | 12/1988 | Katz . |
| 4,803,048 | 2/1989 | Nason . |
| 4,886,071 | 12/1989 | Mehl et al. . |
| 4,917,867 | 4/1990 | Jensen et al. . |
| 4,949,840 | 8/1990 | Brown . |
| 4,979,515 | 12/1990 | Briggs . |
| 5,050,735 | 9/1991 | Levy . |
| 5,156,948 | 10/1992 | Christensen et al. . |
| 5,190,049 | 3/1993 | Briggs et al. . |
| 5,211,286 | 5/1993 | Turner . |
| 5,509,064 | 4/1996 | Welner et al. . |

FOREIGN PATENT DOCUMENTS

WO88/10272  12/1988  WIPO .

OTHER PUBLICATIONS

Anderson, "Home Test Kits for AIDS Blocked," *Nature*, 332:573 (1988).

DeChristophoro, "What is the Stastus of AIDS Antibody Home Test Kits?," *Am. J. Hosp. Pharm.* 43(3):61 (1990).

Pazin, "Counseling must Precede Testing for HIV/AIDS," *Pa.Med.* 94(4): 22–25 (1991).

Pazin, "HIIV–AIDS Post–Test Counseling," *Pa. Med.* 94(5):18,20 (May 1991).

Teamsters Health Center Ltd., Feb. 5, 1992, pp. 1–5.

Phillips et al., "Testing for HIV Infection at Home," *New England J. Med.* 332(19): 1296–1310 (Mar. 11, 1995).

CBS, Inc., Partial Transcript of "60 Minutes" (date unknown).

Search Report for PCT/US94/12623.

United States House of Representatives, "Risks and Implications of AIDS/HIV Testing in Nontraditiona Laboratories and In The Home," Hearing Report, $101^{st}$ Congress, $1^{st}$ Session, Mar. 23, 1989.

U.S. Department of Health and Human Services, FDA, Blood Products Advisory Committee, "Regulator History of AIDS Tests with Home Collection," Thirtieth Meeting, Jul. 18, 1990.

*Primary Examiner*—Jeffrey Stucker
*Attorney, Agent, or Firm*—Leydig, Voit & Mayer Ltd.

[57] ABSTRACT

An anonymous testing system for taking a sample of body fluid to be tested, the sample is acquired in private and sent for analyzation to obtain results. The system comprises a test kit for creating a sample of body fluid, a personal code for anonymously identifying the sample and the person, and an electronic file telephonically created and accessed by the person taking the test and identified by the personal code. The electronic file contains the test results determined by analyzation. There is also a method of anonymously testing of a person's body fluid in private and the results to be anonymously received by the person without having to reveal his or her identification. The method comprises the steps of procuring a test kit for taking a sample of the body fluid. The test kit has a personal code associated therewith and equipment to take the sample. The person uses the equipment to obtain the sample and sends the sample with the personal code to a testing site. The person also creates a personal electronic file telephonically; the file is identified by the personal code. The sample is identified by the personal code. At the testing site, the sample is tested, and the results are updated into the electronic file with a corresponding personal code. The person later accesses the electronic file telephonically to obtain his or her results.

60 Claims, 6 Drawing Sheets

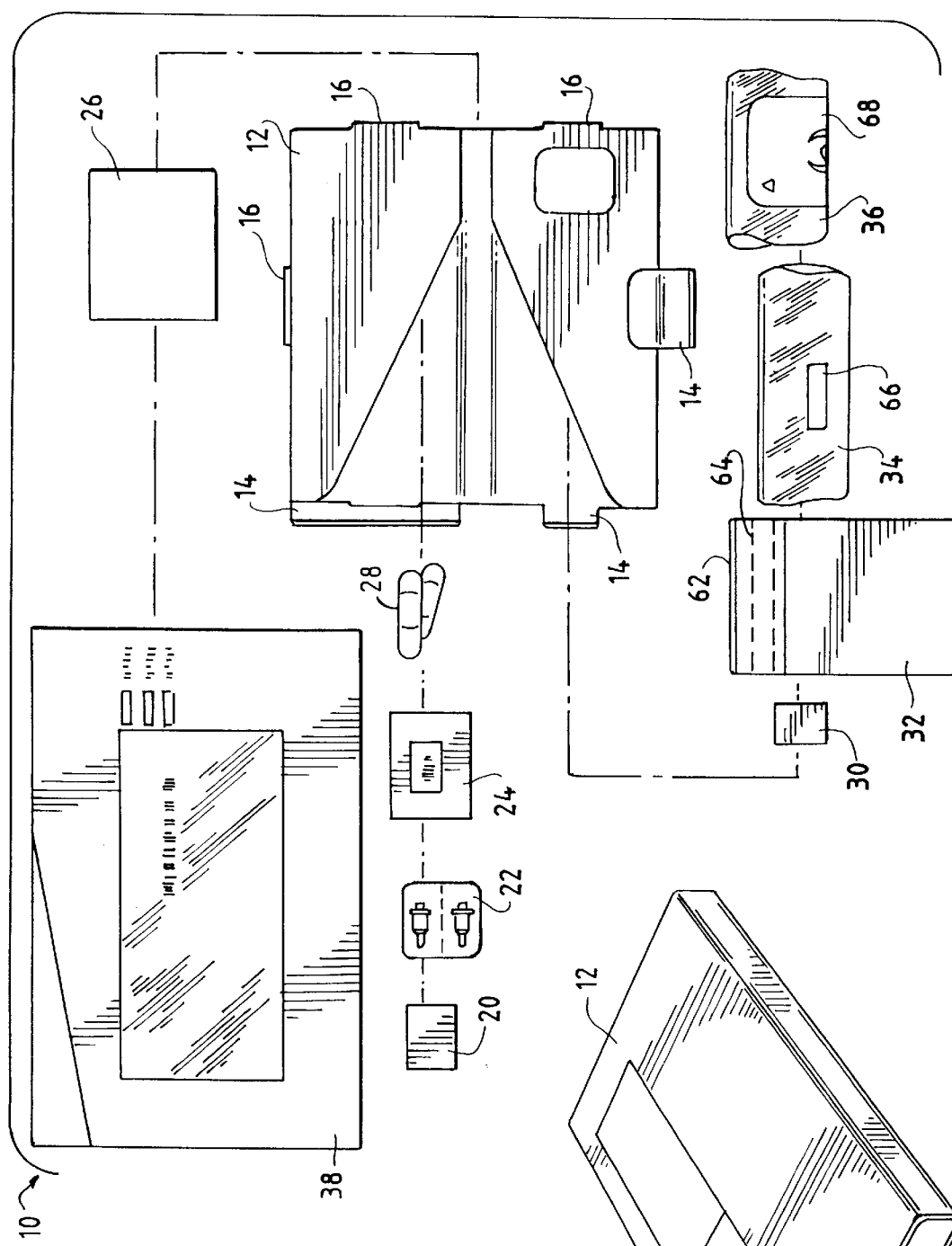
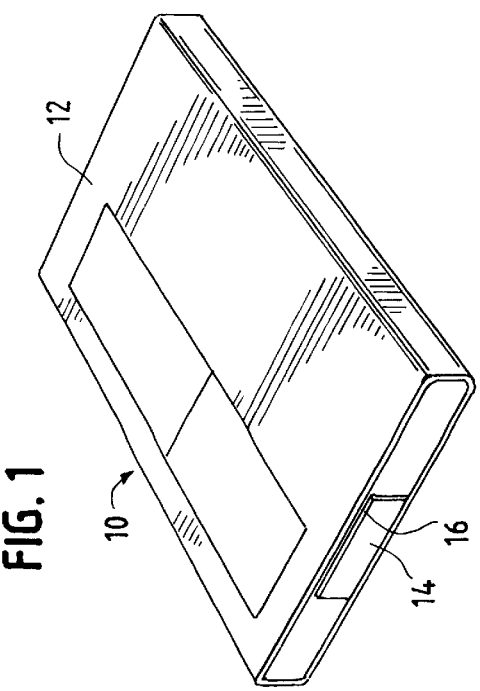

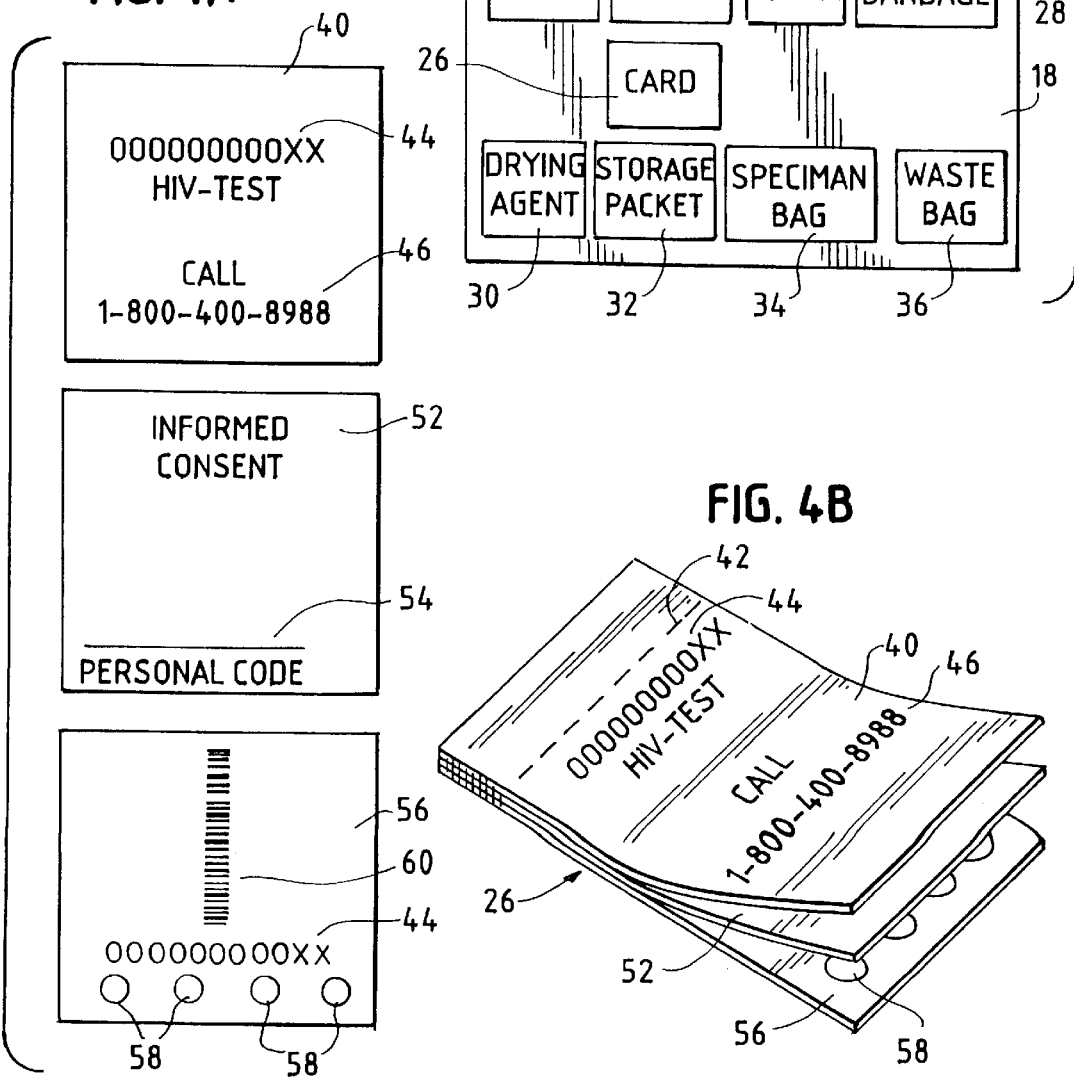

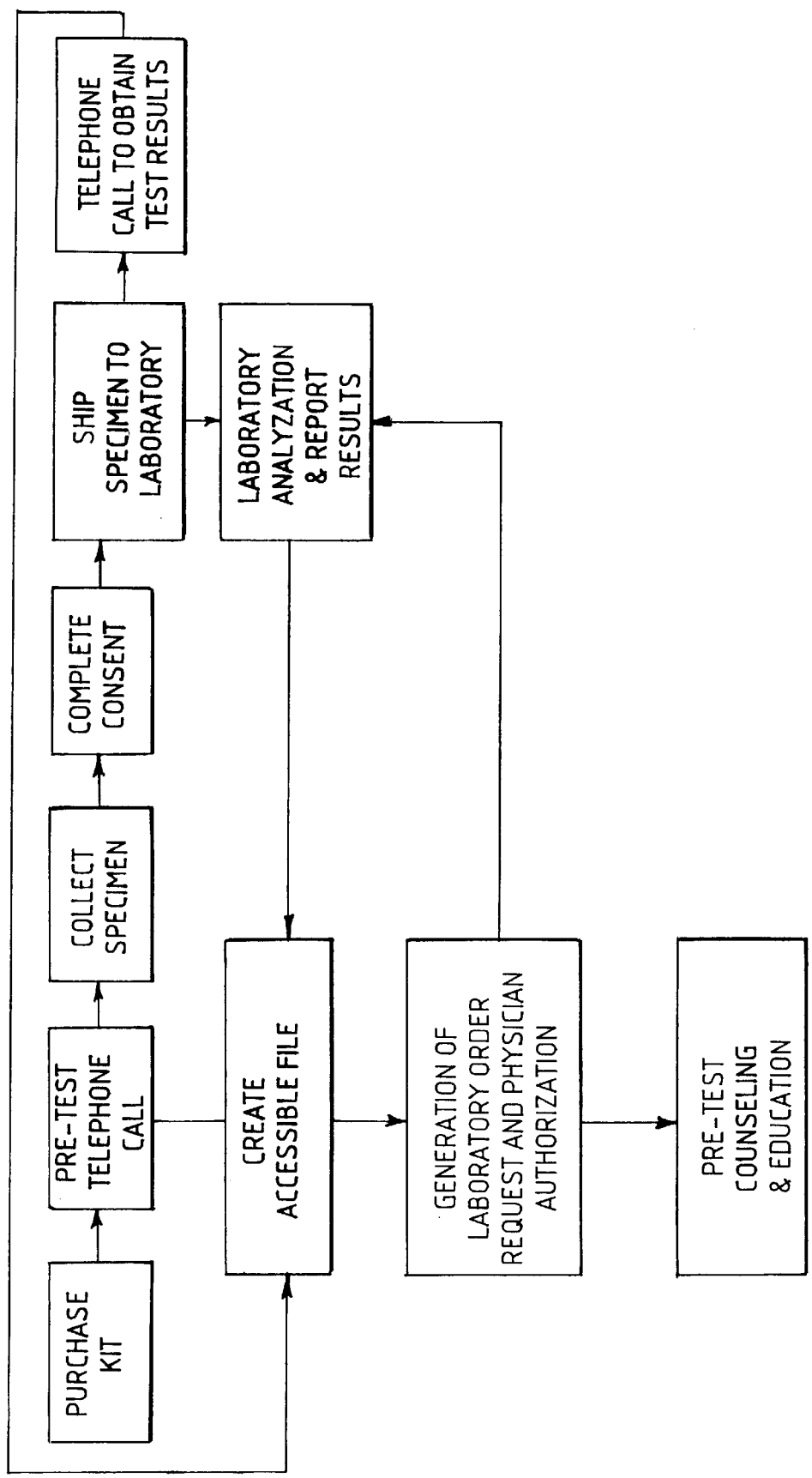

METHOD AND SYSTEM FOR ANONYMOUSLY TESTING FOR A HUMAN MALADY

RELATED APPLICATION

This is a divisional of application Ser. No. 08/877,702, filed Jun. 16, 1997, which application is a continuation of application Ser. No. 08/420,694, now abandoned, filed Apr. 12, 1995, which is a continuation-in-part of copending patent application Ser. No. 08/146,307 filed on Nov. 2, 1993, now abandoned.

FIELD OF THE INVENTION

The present invention relates to a method and system for testing for human malady and, more particularly, to a method and system for testing for the Human Immunodeficiency Virus (HIV) which is responsible for Acquired Immune Deficiency Syndrome (AIDS).

BACKGROUND OF THE INVENTION

Many of today's human maladies are highly contagious, readily transmissible, and, in some cases, medical cures have not yet been discovered. For example, AIDS has become a serious health threat and has reached epidemic proportions around the world. Presently, there is no cure for AIDS or for the HIV virus that causes AIDS. While having the HIV virus does not necessarily mean that a person will contract AIDS, because of its contagiousness and transmissibility, it is important to know whether a person is infected with the HIV virus.

Both HIV and AIDS are not inherited but are acquired. HIV is passed from one person to another as through the transference of body fluids such as infected blood, semen or vaginal fluids. Accordingly, HIV is often transmitted by unprotected vaginal, anal, or oral sexual intercourse, or through the sharing of hypodermic needles by intravenous drug users. Infants can also acquire HIV from their mothers during pregnancy or delivery.

A fundamental step in preventing the spread of HIV and AIDS is to inform those people who are infected about their condition. Hopefully, once someone knows they are infected they will take extra precaution in their activities thereby containing the spread of the disease. While a cure for the HIV and AIDS has not yet been found, the medical community has developed accurate tests to detect the presence of HIV antibodies in the blood stream. The most recognized tests are known as the Enzyme Linked Immunosorbent Assay (ELISA) and the Western Blot tests. By combining these highly effective tests, test results can be approximately 99.7 percent accurate. There are other tests available and more are being developed that can test for HIV antibodies and the AIDS virus.

HIV antibodies develop in the blood stream after someone is infected with HIV. These antibodies can take up to six (6) months to develop before being detected by the ELISA and Western Blot tests. Accordingly, immediate infection with HIV virus is not necessarily detectable.

Even though the tests for HIV are highly accurate, many people are reluctant to have themselves tested. A fundamental reason for this reluctance is fear: the fear of death and the stigma of having AIDS. Not only do people with AIDS have to deal with this devastating and terminal disease, but they also have to deal with the potential that they may be discovered and thereafter severely discriminated against.

The general populace's prejudice and fear stem from many different things. One reason is general discrimination towards homosexual men. The homosexual male population was one of the first communities heavily affected by AIDS. Accordingly, AIDS became known as a gay disease and people with AIDS are assumed to be gay. Also, the repercussions of someone finding out that the person being tested has a particular human malady such as AIDS can result in severe consequences such as loss of employment, loss of insurance, sometimes loss of housing, and even loss of family and friends.

A deeper element to the problem is based in the public's general lack of understanding about how one can contract the HIV virus. Casual contact does not promote the spread of the disease. However, until the public understands this, people with AIDS tend to be ostracized from their community at a time when they need the most support. Adults have been fired from their jobs, and children have been locked out of their schools.

Problems for people with HIV and AIDS are also present in the medical community. People with HIV and AIDS can find it hard to find a doctor that will treat them, and quite often insurance companies are unwilling to pay for the necessary and expensive treatments that AIDS patients require.

Taking into account these factors, the decision to take an HIV antibody test is a difficult choice to make. However, there are many good reasons to do so, such as: a need to know; anxiety relief; protecting oneself; protecting one's sexual partners; protecting one's children; and obtaining early medical intervention.

People are still afraid to take a test, however, for the fear that others will find out if the test is positive. There are procedures to ensure that one's HIV status is protected from others. Confidentiality and the ability of the person taking the test to remain completely anonymous remains a serious problem with prior art test kits. Experts remain of the opinion that confidentiality/anonymity remains a serious concern and a major obstacle when attempting to find a solution to the AIDS epidemic. While testing appears to be the answer, maintaining patient confidentiality/anonymity is the problem. There is no system or method, however, that completely protects the identity of the person who has submitted themselves for HIV tests.

In the past, systems have been developed that attempt to protect individuals from the general dissemination of test results. Medical practices and policies, like the doctor-patient privilege, attempt to shield people with AIDS from embarrassing exposure and public ridicule. There are clinics which have procedures for anonymous testing. These clinics use number identifiers to protect patient confidentiality. However, the patient must appear at the clinic where he or she could be recognized by anyone else at the clinic. Accordingly, complete anonymity is difficult to maintain.

Tests have been developed and marketed that allow people to take a blood sample at home and mail it to a medical laboratory for analysis, e.g., Briggs et al. U.S. Pat. Nos. 4,777,964 and 4,979,515. These tests offer anonymity because the user does not appear at a laboratory, hospital or doctor's office. These tests, however, do require the person taking the test to give the laboratory his or her name and address. Thus, complete confidentiality/anonymity for the person being tested is lost thereby discouraging people from taking the test.

Furthermore, the previous personal testing kits have only required the user to supply one blood sample. While often this is sufficient for accurate results, sometimes more than one blood sample is required because multiple tests are needed. It is important to make sure that the results to HIV antibody tests are accurate because of the severe consequences, e.g. death and discrimination, of a positive result.

Accordingly, a medical testing system is needed that is particularly designed to test for the HIV virus and provide the complete confidentiality that allows the user to be completely anonymous. The test should also supply the medical lab with enough of the test specimen to ensure that the test result is as accurate as possible. The presently described invention addresses these mentioned needs.

SUMMARY OF THE INVENTION

In view of the above, and in accordance with the present invention, there is provided a method and system of testing for a human malady in private. One such human malady would be HIV. To overcome the heretofore known confidentiality/anonymity problems associated with the prior art kits, a salient feature of the present invention concerns privately conducting the test and then, without having to reveal their identity, allowing the person taking the test to anonymously and confidentiality obtain the results of the test. The methodology of the present invention involves procuring a kit that is capable of taking a suitable test specimen from the person being tested. The kit has a unique personal code associated with it and all the necessary equipment for the person taking the test to be able to obtain the test specimen in private. The person taking the test proceeds by creating or activating a personal electronic file through a software program in a computer system that can be both created and subsequently accessed anonymously and remotely from a telephone. The electronic file that is set up is identified only by the personal code assigned to the kit. Because the file is created telephonically, the identity of the person taking the test is unknown to others, thus, protecting the confidentiality for and offering complete anonymity to the person taking the test.

According to one aspect of the present invention, pre-test counselling regarding the test and the test results is offered to the person taking the test upon creation of the electronic file. The pre-test counselling is an opportunity for the person taking the test to seek assistance in the form of counselling to cope with the possible results that could result if the testing reveals a positive result.

According to another aspect of the present invention, when the person taking the test anonymously activates the personal code thereby creating the electronic file, the system of the present invention generates an order request form for the laboratory. The order request form is automatically generated and authorizes the laboratory to perform analyzation or testing of the specimen identified by the anonymous code on the specimen.

The person taking the test uses the equipment provided in the kit to obtain a test specimen. In the situation where the person taking the test is concerned about AIDS, the test specimen is often a blood sample but can also be another body fluid like saliva or urine. Once there is a test specimen, the next step is sending the test specimen for analyzation; the test specimen is sent with only the personal code to identify the person taking the test.

Upon receipt of the test specimen, the laboratory matches the test specimen with the order request form that was automatically generated by the system of the present invention when the person taking the test created the personal electronic file. In the situation where the person taking the test is concerned about HIV, the laboratory analyzes the test specimen to determine if the HIV antibodies are present therein. Other tests can be performed on the test specimen to detect a variety of diseases. Once the analyzation step is completed, the electronic file identified by the personal code that corresponds to the personal code of the test specimen is updated by adding the results.

After a sufficient period of time for analyzation and adding the results to the personal electronic file has elapsed, the next step for the person seeking the test results involves telephonically accessing the personal electronic file through the telephone operated software program using the personal code, thereby obtaining the test results while maintaining absolute anonymity/confidentiality for the person taking and seeking those test results.

Depending on the results of the test, the telephone operated software directs the person to the appropriate source to receive the results. For example, if the test results show the presence of a human malady, the person taking the test is told the results and is offered counselling by a professional counselor who does not know the identity of the person. On the other hand, if the test results fail to show or detect the particular human malady that was being tested for, the computer system allows the individual to be informed of such test results by the telephone operated software program. Moreover, the person taking seeking the results of the test is encouraged to speak to a counselor if there is any reason to do so.

The test system herein permits anonymous testing for a particular human malady, and the system includes a kit having the necessary equipment for producing a suitable test specimen from a person being tested which is capable of being transported from one location to another location for analyzation. The Lit allows the specimen to be collected in private. To maintain anonymity, a personal code identifies the person being tested and the test specimen. An electronic file is created and accessible by the person being tested and is identified by the same personal code. The electronic file has entered into it the results of the analysis after the test specimen is analyzed.

As mentioned above, the test kit is equipped with all the proper equipment that an individual will need to acquire a test specimen. When the kit is used to test for HIV, the equipment in the kit will be used to obtain a sufficient amount of a body fluid that can be subsequently analyzed for HIV antibodies.

When the body fluid to be analyzed or tested is blood, the kit is equipped with an alcohol swab to clean an area of the skin, preferably the tip of the middle or ring finger, before the blood sample is taken, and at least two lancets that can puncture the skin so that blood can be acquired. A sterile gauze pad is provided to clean away the first drop of blood which is not suitable for the blood sample. The blood sample is produced by placing enough blood on a specially designed blood specimen collection card provided in the kit to fill preferably four specimen spots.

In one form of the invention, the collection card is configured as a three part card. The first part of the card has printed thereon the personal code and a telephone number that is used by the person being tested to create the personal electronic file. The second part is an informed consent form with an area to be anonymously filled in by the person being tested with the personal code. The third part is special paper with specimen spots outlined thereon for the person being tested to create specimens for testing. The test kit further includes at least one bandage to protect the puncture after the blood sample is produced.

To protect the collection card and, more particularly, the specimen from contamination, the kit is preferably supplied with a foil lined envelope wherein the individual inserts the collection card and a drying agent. The foiled lined envelope is preferably placed in a specially marked specimen bag that is also closed. That equipment that was used to conduct the test is preferably in another specially marked waste bag that is also closed. The bag or container holding the specimen and the waste bag are placed in a container, which is then placed in a mailing envelope and sent for analyzation and disposal, respectively. Alternatively, the waste can be disposed of locally.

Obtaining or procuring a body fluid other than blood, for example, saliva, for the test specimen is likewise intended to be within the spirit and scope of the present invention. When the body fluid or test specimen is saliva, the kit is equipped with an oral specimen collection apparatus. The oral collection apparatus generally includes a small absorbent pad on a suitably configured holder. During use, the holder is placed into the mouth cavity of the person being tested to procure a test specimen of body fluid suitable for the intended testing purposes. After a suitable test specimen of body fluid is obtained, the absorbent pad is sent off for analyzation preferably in a vial having a personal but anonymous code imprinted thereon. With this test kit embodiment, the above-mentioned first and second parts of the collection card are provided with the kit as well as those components to facilitate delivery of the test kit to the laboratory for analyzation.

These and numerous other objects, aims and advantages of the present invention will become readily apparent from the following detailed description, appended claims, and the accompanying drawings.

BRIEF DESCRIPTION OF THE DRAWINGS

FIG. 1 depicts an outer container for holding equipment suitable for obtaining a suitable test specimen arid related equipment of the present invention;

FIG. 2 illustrates the container of FIG. 1 in an open state;

FIG. 3 illustrates one form of equipment that can be used to collect a suitable test specimen;

FIGS. 4A & 4B are detailed drawings of one form of specimen collection card;

FIG. 5 is a block diagram schematically illustrating one operating format of the testing system of the present invention;

DETAILED DESCRIPTION OF THE PREFERRED EMBODIMENT

Figure 6:
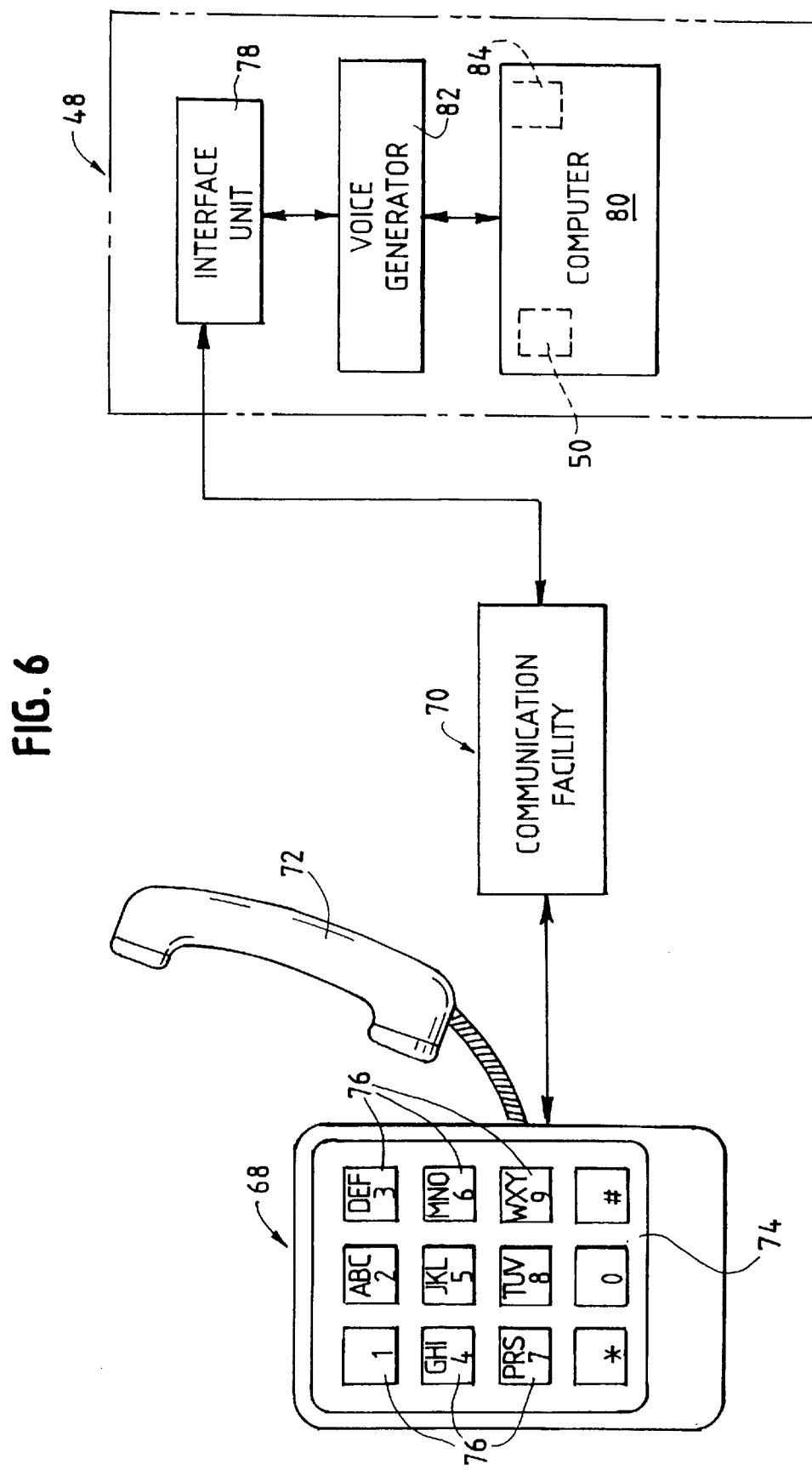
FIG. 6 is a block diagram of a system constructed in accordance with the present invention.

While the present invention is susceptible of embodiment in various forms, there is shown in the drawings and will hereinafter be described preferred embodiments of the invention with the understanding that the present disclosure is to be considered as setting forth exemplifications of the invention which are not intended to limit the invention to the specific embodiments disclosed.

Referring now to the drawings, wherein like reference numerals indicate like parts throughout the several views, the present invention is an anonymous testing system which utilizes a kit 10 as a primary component thereof. As shown in FIG. 1, kit 10 includes an outer box or container 12 used to package and mail the kit 10. Multiple tabs 14 inserted into multiple slots 16 are provided to keep the box 12 in its folded and secure position as shown in FIG. 1. FIG. 2 illustrates how when tabs 14 are removed from slots 16 box 12 can be unfolded to reveal the enclosed equipment which are used for the anonymous medical test.

At least a portion of the equipment in the kit preferably comes confined in a sealed clear plastic bag 18 as shown in FIG. 3. The clear plastic bag allows the person being tested to examine the contents of the test to determine if all the necessary parts are provided.

FIGS. 2 and 3 schematically illustrate those testing components that are preferably provided with the kit 10 for securing a blood specimen. In those situations where a blood specimen is collected for analyzation or testing purposes, the components provided with the kit 10 preferably include: 1) an alcohol swab 20; 2) a lancet 22; 3) a gauze pad 24; 4) a blood specimen collection card 26; 5) a bandage 28; 6) a drying agent (desiccant) 30; 7) a storage packet 32; 8) a specimen bag 34, and 9) a waste bag 36. Alternatively, and as will be readily appreciated, the kit 10 can include other equipment for collecting another suitable test specimen, i.e., saliva or urine without detracting or departing from the spirit and scope of the present invention. A mailing envelope 38 may also be provided with the kit 10 to facilitate returning a test specimen for analyzation.

Alcohol swab 20 is preferably a 1¼ inch by 2⅝ inch single fold, nonwoven applicator swab saturated with 70% isopropyl alcohol. To prolong the usefulness, swab 20 is preferably packaged in a foil tear-open packet, and can be of the type produced by Baxter Healthcare Corporation. Alcohol swab 20 is used to clean an area of skin from which blood will be drawn.

The lancet 22 is preferably a single use lancets with a blade width of 1.0 mm and blade depth of 2.2. mm such as Becton Dickinson Microtainer Brand "Yellow" Safety Flow Lancets. Lancet 22 is used to puncture the cleaned skin of the user.

Gauze pad 24 is preferably a 2 inch by 2 inch sterile 12-ply sponge pad of 100% cotton USP Type VII gauze like that manufactured by Johnson & Johnson. Gauze pad 24 is used to clean and dry the skin around the puncture area.

The bandage 28 provided are preferably 1 inch by 3 inch sterile wrapped adhesive strips of the type manufactured by Kendall Futuro as Curad® brand bandages. The bandage 28 is used to cover the punctured skin after a blood sample is taken.

The drying agent 30 can be any desiccant, but is preferably a silica gel like the one produced by U.D.G of Belen, N. Mex. and marketed as Sorb-It®.

FIGS. 4A and 4B schematically illustrate one form of blood specimen collection card 26 which is preferably configured in a diagnostic form having three (3) parts. The first part is a removable top sheet 40. Perforations 42 are preferably provided to enable the person being tested to remove the top sheet 40 from the remainder of the collection card 26. Printed on top sheet 40 is information that the person being tested needs to retain after the remainder of the collection card 26 is sent for analysis. This information includes a personal code 44 and a telephone number 46.

Personal code 44 is used to identify the test specimen and the person being tested rather than a name and/or address. The personal code 44 is assigned so that each kit has a unique code 44 associated therewith. Because each number is unique, the person being tested can remain completely anonymous while having his or her blood specimen analyzed.

As shown in FIG. 4A, the personal code 44 is preferably an eleven (11) digit number. Nine digits, indicated-by "0"s, are randomly assigned and the remaining two digits, indicated by "X"s, are used as a check sum to assure accuracy each time the number is used. It should be noted that any other system of identification can be used as long as the indicators assigned to each kit 10 do not reveal the identity and thereby advantageously maintaining confidentiality of the person taking the test.

The telephone number 46 provides access to a computer system generally designated in FIG. 6 by reference numeral 48 wherein a personal electronic file 50 is created and to which access is provided to allow a laboratory to report the test results thereto and to which the person being tested has subsequent access, as described below, to obtain the laboratory test results without having to personally appear before or otherwise reveal their identity to anyone thereby maintaining the anonymity/confidentiality which is such an important concern to those persons taking the test.

The second part of collection card 26 is an informed consent form 52. The informed consent form 52 contains a series of statements that the person being tested must read, understand, and acknowledge before a laboratory can perform any test on the specimen. The informed consent form 52 is returned along with the specimen. The consent form 52 has a space 54 which the individual fills in thereby acknowledging having read and understood the statements. To keep the anonymity of the person being tested, the user fills in the space 54 with the personal code 44.

In its illustrated form, the third part of collection card 26 is a blood specimen sample sheet 56. Sample sheet 56 is at least in part a cotton fiber filter paper preferably like that manufactured by Schleicher and Schuell® as #903™. Sample sheet 56 has a blood collection area specifically designated thereon. In the illustrated embodiment, four similarly shaped sections 58 are outlined thereon for deposit of a specimen in each section. The sections 58 are outlined using black biological ink so that the ink will not interfere with the specimen and an accurate test result can be obtained. It is best if the shapes are circles. The sections 58 are spaced adequately apart so that the four different specimens will not be commingled and that acquiring the specimens will not be too difficult. Alternatively, a single, somewhat larger, collection area may be designated on the collection card 26.. The single collection area is sized such that after the card 26 is received at the laboratory four different specimens can be punched or otherwise removed from the one single area to provide the four specimens for testing purposes.

The blood specimen sample sheet 56 further includes a bar code 60 having the same personal code 44 as was randomly assigned to the top sheet 40. The bar code 60 is used by the laboratory to identify the specimen as belonging to the person being tested who has been assigned the corresponding personal code 44. Accordingly, the person being tested and assigned the personal code 44 can be updated with the results of the analyzation. As will be appreciated, because no personal identifying information concerning the person being tested can be derived from the code 44 available to the laboratory, confidentiality of the person taking the test and that person's anonymity is protected against someone at the laboratory inadvertently or otherwise discovering the identity of the person taking the test.

In one form of the invention, the storage packet 32 included with the kit 10 is preferably a foil lined opaque envelope. As shown in FIG. 2, a top edge 62 of the packet 32 has an adhesive strip 64 covered by removable silicon strip. The storage packet 32 is sized to hold the collection card 26 therewithin. That is, after the test specimen has been completed, the card 32 containing the test specimen is inserted within the storage packet 32 along with the drying agent 30.

After the collection card 26 and drying agent 30 are deposited within the storage packet 32, the silicon strip is removed from the adhesive strip 64 and the top edge 62 is folded down so that the adhesive strip 64 sticks to the outside of the storage bag 32 thereby closing the storage packet 32 with the specimen card enclosed therein. Specimen bag 34 is preferably a clear plastic bag that can be securely closed along its upper edge and is large enough to hold the storage packet 32. On the outside surface of the specimen bag 34, there is a label 66 preferably stating "specimen" so that the purpose and contents of the bag are clearly stated.

In the illustrated embodiment, the bag 36 included with the kit 10 is also a clear plastic bag that can be securely closed along its upper edge. Waste bag 36 preferably has a label 68 stating "Caution Biohazard" along with the typical biohazard symbol so that the contents of the bag 36 are readily identified as medical waste. Bag 36 is large enough to hold the remaining and used elements of the test system 10, e.g. the lancets 22 and gauze 24 that were used by the person taking the test to obtain a test specimen.

Mailing envelope 38 is preferably a typical express mail type envelope used by e.g., Federal Express® or the United States Postal Service. The mailing envelope 38 should be sufficiently large enough to hold the box 12 therein for sending to the laboratory.

An appreciation of the philosophical operation of a test system according to the present invention may be enhanced by considering an exemplary operation thereof as schematically represented in FIG. 5. To begin, the user purchases the kit 10 from a suitable supply source. In the privacy of their own home, the user opens the box to reveal the testing equipment (See FIGS. 1 and 2). The kit 10 can also contain an instruction booklet (not shown) which serves to help the person being tested obtain a specimen and answer any questions.

Initially, the person being tested should create an accessible electronic file 50 in the computer system 48 (FIG. 6). In accordance with the present development, the person being tested uses a telephone station 68 to interface with the computer system 48 as through a conventional communication facility 70 to create the accessible electronic file 50 in the computer system 48 and that is identified solely by the personal code associated with the kit 10 obtained by the person taking the test. In the illustrative form shown in FIG. 6, the communication facility 70 comprises a conventional telephone facility and the telephone station 68 is preferably a conventional telephone including a hand piece 72 (microphone and earphone) and a panel 74 provided with an array of manually operated buttons 76.

As is conventional, alphabetic and numeric designations are provided on the buttons 76 of the telephone station 68. For example, several of the buttons 76 carry both letters and a number thereon. Consequently, the buttons 76 readily accommodate entry of the personal code 44 to create the personal and accessible file 50 in the computer system 48. The user will find the assigned code 44 on the top sheet 40 of the collection card 26. Also on the top sheet 40 of card 26 is the telephone number 46 the person being tested calls to activate the personal code 44. By using the push buttons 76 of the telephone 72, the user registers or creates the electronic file 50 in the computer system 48.

Considering the computer system 48 in somewhat greater detail, the communication facility 70 is coupled to an interface unit 78. The interface unit 78 is coupled to a suitable computer 80 through a voice generator 82. Generally, the computer 80 performs several distinct and separate functions such as qualifying a caller under the influence of an automated computer program 84. The computer 80 furthermore receives detailed data from the caller and stores the data in the electronic file 50 identified by the personal code associated with each kit. As will be appreciated, the voice generator 82 functions to selectively provide voice messages through the interface unit 78 and the communication facility 70 to prompt certain responses from the caller through use of the telephone station 68. Thus, the identity of the caller is maintained confidential throughout the testing procedure.

Returning to FIG. 5, an important feature of the present invention concerns the ability of the computer system 48 to generate a laboratory order request that is automatically delivered to the laboratory where the specimen is to be sent for analyzation. Notably, the laboratory order request is preferably generated by the computer program 84 conjointly with creation of the accessible electronic file 50 and is identified only by the code associated with the personal file. The laboratory order request provides the laboratory that is conducting the analysis of the test specimen with a physician's authorization to conduct the analyzation techniques on the test specimen forthcoming from the patient being tested. Thus, the laboratory is both alerted as to the forthcoming delivery of a test specimen and, accordingly, a physician's authorization is on file when the test specimen is received to reduce the time lapse required for the laboratory to report the test results to the accessible file.

When the person being tested telephones to create the electronic file 50 in the computer system 48 by activating the personal code 44, the telephone automated software program 84 of the computer system 48 collects demographic information, and the person being tested is preferably offered pre-test counseling. The demographic information will not include any information that would divulge the true identity of the person being tested. The type of information sought concerns the sex and age of the person being tested, risk factors, and the person's zip code and is inserted into the electronic file 50. Organizations like a local health department and/or the Center for Disease Control in Atlanta, Ga. can then use this information for statistical purposes in its monitoring of the AIDS epidemic.

Figure 7A:
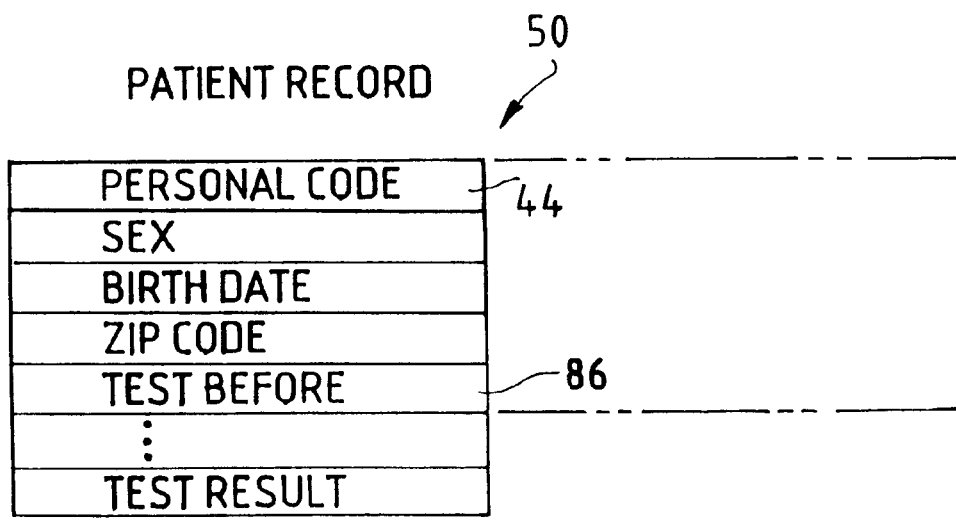
FIGS. 7A & 7B illustrate some elements of an electronic file forming part of the present invention.
Figure 7B:
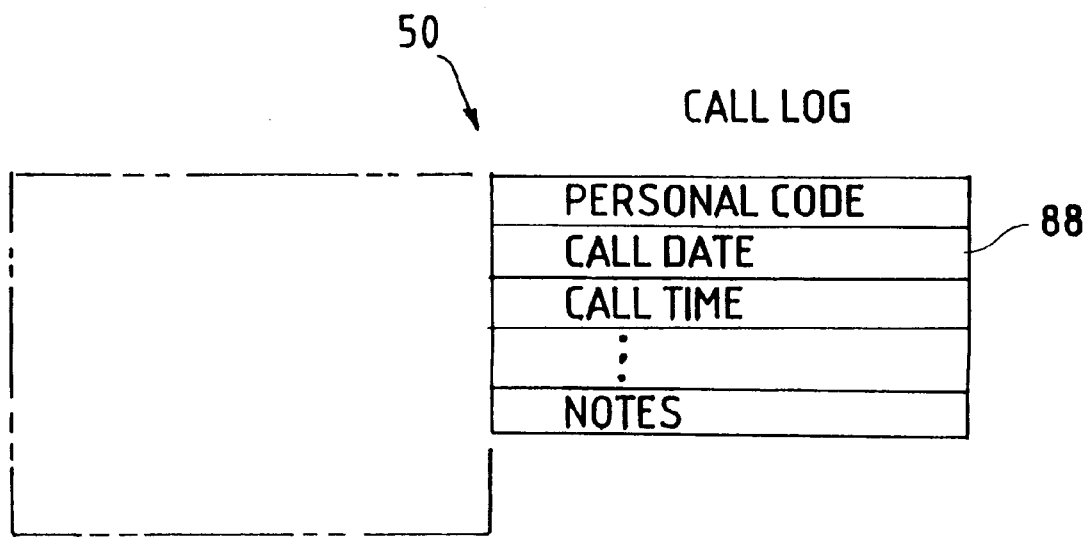

FIGS. 7A & 7B schematically illustrate the elements of the personal electronic file 50 that are created by the person being tested when he or she telephones the computer system 48 to activate the personal code 44 assigned to the kit 10. As will be appreciated by those skilled in the art, the electronic file 50 is a computer database file that holds all the relevant non-identifying data about the person being tested. As shown in FIGS. 7A and 7B, the electronic file 50 has at least two subfiles; a patient record 86 and a call log 88. The patient record 86 holds relevant information about the person such as the personal code 44, the sex, birth date, zip code, risk factors, whether the person has been tested before, and test result. The call log 88 is set up for each time that the user calls. Each call log 88 is identified by the users personal code 44, and also designates the date and time of each call. There is also space for a counselor to put notes about each call.

The pre-test counseling is an opportunity to help the person being tested cope with the possibility that the results from the test will be positive. A counselor will ask a series of questions like, "What do you expect your test results to be?" "What would you do if your test results are positive?" "Who could you rely on for support if your test results are positive?" etc.

Returning to FIG. 5, after establishing the electronic file 50 in the computer system 48, the person being tested collects a specimen for testing purposes. In those instances where a blood specimen is to be collected, the person taking the test selects and cleans a skin area with soap and water. To assure cleanliness, the alcohol swab 20 is preferably used to further clean an area. The skin area can be from any part of the body, but the tip of the middle or ring finger is preferable. After the finger is cleaned, the person being tested should dry the finger tip with the sterile gauze pad 24.

The person being tested opens a lancet 22 to puncture the cleaned area thereby producing a flow of blood. In order to effectively use the lancet 22, the person being tested should stabilize the finger such as on a flat hard surface and position the lancet 22 between the fore and middle fingers of the opposite hand. The lancet 22 is then placed against the pad of the finger tip thereby causing a dimple. When the person being tested is ready, the lancet's plunger is depressed and held for a split-second. This motion causes the blade of the lancet to puncture the skin thereby producing a flow of blood. After the puncture is created, the lancet is removed from the finger area, and the first drop of blood is wiped away by the sterile gauze pad 24. Another drop of blood should develop soon thereafter.

Next, the person being tested applies the drops of blood developing on the finger tip to the sample sheet 56 of the collection card 26 by gently touching the finger to the one or more specimen sections 58 after a large drop of blood has developed. The person being tested should keep the sample sheet 56 in contact with the finger to allow a sufficient quantity of blood to soak through sample sheet 56 and fill the specimen section 58 on the card 26.

After filling the specimen section 58 on the card 26, the person being tested can bandage the area puncture with the bandage 28 that is provided.

Prior to sending the specimen to the laboratory, the person being tested must also acknowledge that he or she has read and understood the informed consent form 52 on the collection card 26. The informed consent form 52 has a statement informing the user about the test, the meaning of the results, and authoring a medical laboratory to test the blood specimen sent to it for the presence of HIV antibodies. In order to protect anonymity, the person being tested is reminded to fill in the consent form 52 with the assigned code 44 rather than sign his or her name. The consent form 52 should not be removed from the collection card 26.

After procuring a test specimen and completing the consent form 52, the specimen is prepared for delivery to the laboratory for analysis. In the example of the blood collection card 26, the drying agent 30 is inserted into the storage packet 32 and followed by the collection card 26. The silicon strip is removed, and the top edge 62 of the storage package 32 is folded over so that the adhesive strip 64 sticks to the outside surface of the storage packet 32 thereby closing the collection card in the storage bag 32. After the storage packet 32 is closed, the person being tested inserts it into the specimen bag 34, which is closed along its top edge.

In a most preferred form of the invention, those materials that were used during the testing process are likewise returned to the laboratory along with the collection card for proper disposal thereof. For example, after the test specimen is obtained from the person being tested, the remaining equipment used during the test is inserted into the waste bag 36. The items to be placed into the waste bag 36 preferably include the used alcohol swab 20, the lancet 22, the used gauze pad 24, and any wrappers or packaging. The only thing that ought to remain outside either the specimen bag 34 or the waste bag 36 should be the top sheet 40 which the user needs for future reference. Alternately, the equipment and related material used during the testing process with the exception of the test specimen can be disposed of locally.

The person being tested then places the specimen bag 34 and the waste bag 36 into the box 12. The flaps 14 are inserted into the slots 16 so that the box is secured shut. Then, the person places the box 14 into the mailing envelope 38 so that the laboratory receives the collection card 26 and the waste for testing and disposal, respectively.

As mentioned above, and as shown in FIG. 5, when the person being tested creates the personal file 50 in the computer system 48, a laboratory request order is automatically generated by the computer program 84 and sent to the laboratory wherein the test analysis is to be conducted. Accordingly when the test specimen is received at the laboratory it is matched with the laboratory request order that has the same personal code thereon and along with the physician's authorization analyses of the test specimen can begin immediately at the laboratory thus reducing the time required to report the results to the electronic file 50 in the computer system 48.

It will be appreciated that there are numerous other testing techniques that are commercially available for detecting the presence of the HIV virus in addition to those mentioned and described above. Some such commercially available HIV tests use other types of body fluids such as saliva or urine as suitable test specimens. The advantages of using a body fluid like saliva or urine include having a non-invasive test, which could potentially make AIDS testing more acceptable and plausible. Testing a body fluid like saliva or urine may also be less expensive than those tests requiring a blood specimen for testing purposes. Accordingly, it is within the spirit and scope of the present invention to provide kit 10 with equipment capable of collecting a suitable test specimen other than blood.

For example, rather than providing equipment for collecting a blood specimen as discussed above, kit 10 could alternatively include an oral specimen collection apparatus. One commercially available form of oral collection that readily lends itself to use with the present invention is that marketed and produced by Epitope medicare Products Division of Beavertown, Oreg. under the name OraSure®.

Suffice it to say, the OraSure® device includes a small absorbent pad on a suitably configured holder. During use, the pad is preferably placed between the lower cheek and gum of the person being tested for a given period of time during which the pad absorbs body fluid and, more particularly, mucosal transudate samples. After the body fluid is collected, the absorbent pad is placed in a specimen collection bag that may be similar to the bag 34 mentioned above. Alternatively, the collection pad and holder are placed in a suitable vial with a personal code printed thereon. The vial is then packaged in the specimen bag 34, and inserted into the mailing envelope 38 for transport to a suitable testing and analyzation facility.

When an oral specimen collection apparatus is used to procure a test specimen, a collection card, similar to the collection card 26 discussed above, is enclosed together with the specimen collection apparatus to the testing facility. The collection card enclosed with the oral specimen collection apparatus is preferably configured as a two-part form including a top sheet and a consent form. The top sheet of the two-part form is substantially similar to the top sheet 40 described above and includes the personal code that is identical to that imprinted on the vial captively holding the specimen and further includes a telephone number of the testing facility. The informed consent portion of the two-part form is substantially similar to the informed consent from 52 mentioned and described above.

Regardless of the type of specimen sent to the laboratory for analysis, the user should wait a number of days before seeking the results. When the laboratory receives the test sample, it will perform suitable test or tests thereon to detect for HIV antibodies. When the results of the test are known, the laboratory will update the electronic file 50 created by the person being tested that corresponds to the bar code 60. After the electronic file 50 is updated, and as shown in FIG. 5, the person taking the test can access the test results. It should take approximately seventy-two hours after the laboratory has received the collection card 26 to update the electronic file 50.

Figure 8:
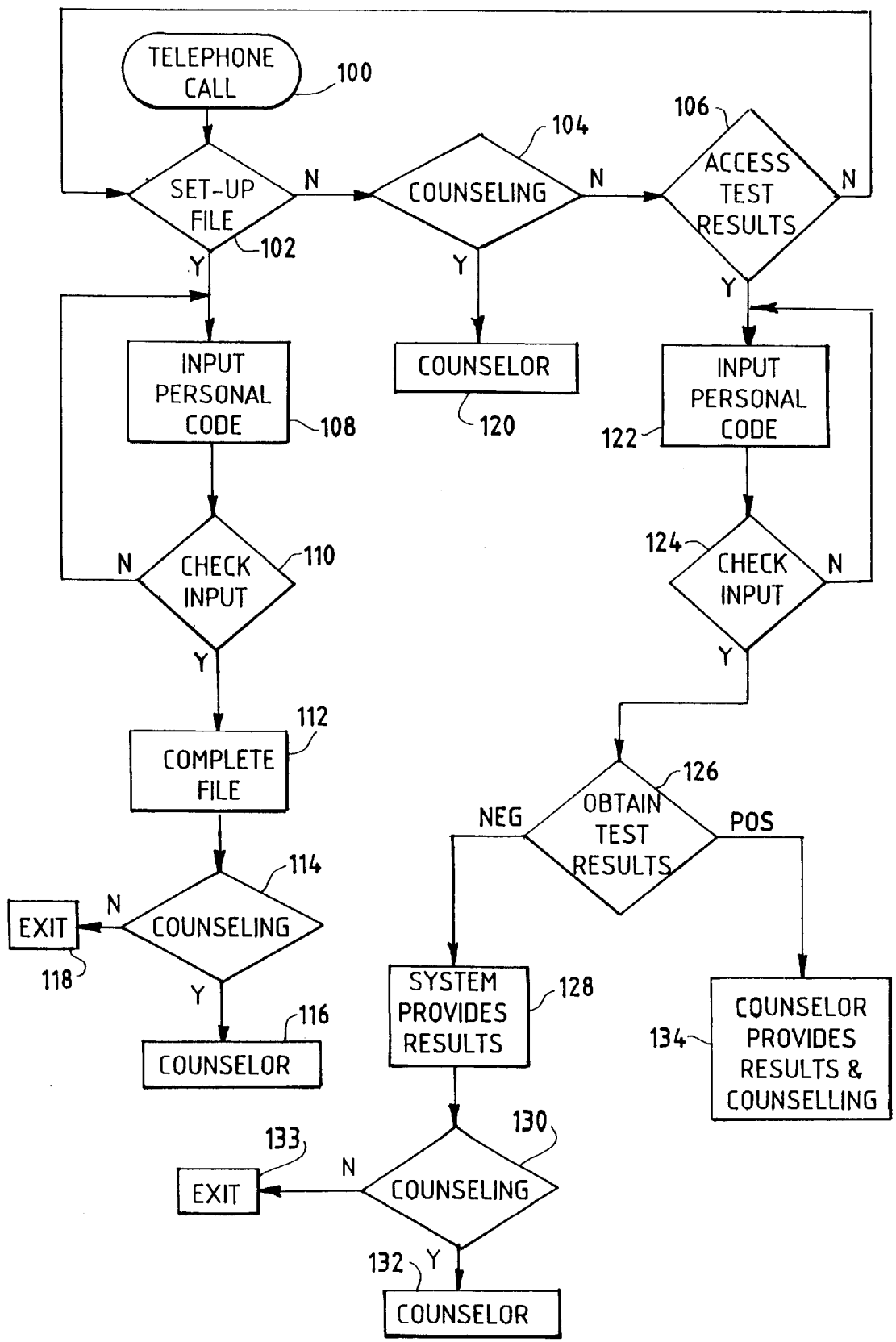
FIG. 8 is a flow chart schematically representing operation of a telephone operated automated software program of a computer system associated with the present invention.

In order to obtain the test results, the person will call the phone number 46, which can be found on the retained top sheet 40 of the collection card. As shown in FIG. 8, and to further protect the confidentiality/anonymity the person taking the test, the caller is provided access to the test results only through providing the code associated with this particular caller. Only after entering the correct code is access to the test results provided to the caller. If the test results are negative, the telephone operated computer program or software 84 of the computer system 48 will inform the by person being tested of the negative results.

On the other hand, a counselor will inform the user of the positive results. This way the user can be told how to get the proper medical attention and to determine if the user has possibly infected others with the HIV virus. At no point in the process is the identity of the user revealed. Also if the test results are positive, the local health department and/or the Center for Disease Control can be informed.

The telephone automated software program 84 in the computer system 48 has been developed for people to create and access their electronic file 50. When a person calls the telephone number 46, the person accesses the telephone automated software program 84 and receives prompts from the voice generator 82 of the computer system 48 on how to proceed.

FIG. 8 is a flow diagram illustrating the steps of the telephone automated software program 84. The sequence of operations of the program 84 is represented to be initiated in FIG. 8 at step 100 by the person using the telephone station 48 to call the telephone number provided with the specimen collection kit 10 to access the computer program 84 in the computer system 48. After accessing the computer program 84 in the computer system 48, the voice generator 82 formulates questions asking the person taking the test whether they: desire to set-up an electronic file at step 102, desire counselling as at step 104 or desire to access test results as at step 106.

In the instance where the caller wants to initially set-up an electronic file 50 in the computer system 48, and acting on instructions from the voice generator 82, the caller would input a personal code as at step 108 by pushing those buttons 76 on the telephone station 68 corresponding to the code 44 associated with the kit 10. Notably, with the present invention, it is not necessary for the person taking the test to appear or surrender their identity to anyone to set the file or obtain the results of the testing. After the code 44 is entered at step 108, the computer program 84 checks the number entered against a predetermined valid set of codes as at step 110. If the code entered at step 108 is invalid, the voice generator 82 instructs the caller to reenter the code and, thus, returns the computer program 84 to step 108. To protect the confidentiality/anonymity of the caller, a predetermined number of attempts at entering the correct code are provided before the computer system 84 terminates the telephone call.

If the caller responds with a proper code, the computer program proceeds to allow the caller to complete the electronic file as at step 112. As mentioned above, completing the file 50 involves providing additional statistical data none of which is indicative of or revealing of the identity of the person being tested. Thus, the confidentiality of the caller is completely protected.

Upon completion of the electronic file 50, the caller is queried whether they want to seek counselling as at step 114. If the caller does seek counselling, the program shifts to step 116 whereat a counsellor provides the caller with appropriate counselling. On the other hand; if the caller does not want counselling, the program 84 shifts to step 118 whereat the computer system terminates the call.

If the person calling does not seek to set-up or create a file, or in an instance where the caller may have already created the file 50 in the computer system, but wants counselling, the program can be shifted to step 104. In response to a prompt from the caller indicating that counseling is desired, the program 84 shifts to step 120 where professional counselling is provided to the caller.

On the other hand, if the person being tested is calling to access the test results, the caller prompts the program 84 to proceed to step 106. At step 106, the caller responds to prompts from the computer program to obtain results as by inputting the correct code known only to the caller. At step 122, the caller would input the personal code as by pushing those buttons 76 on the telephone station 68 corresponding to the code 44 associated with the kit 10. After the code 44 is entered at step 122, the computer program 84 checks the code entered against a predetermined valid set of codes as at step 124. If the code entered at step 122 is invalid, the voice generator 82 instructs the caller to reenter the code and, thus, returns the computer program 84 to step 122. To protect the confidentiality of the caller, a predetermined number of attempts at entering the correct code are provided before the computer system 84 terminates the telephone call.

If the caller responds with a proper code at step 124, the computer program proceeds to allow the caller to telephonically obtain the test results as at step 126. As will be appreciated, the test results were previously entered to the electronic file 50 by the laboratory. Notably, however, the laboratory only identified the test specimen through the code and no personal identifying information or disclosure has been required to be made to the laboratory that could lead to the identity of the person being tested thereby completely protecting the anonymity and confidentiality of the person being tested.

If the test results reported by the laboratory are negative, the program 84 in the computer system 48 operates the voice generator 82 to so inform the person calling for the results as at step 128. Thus, with the system of the present invention, the person taking the test does not surrender their confidentiality/anonymity to obtain the results of the test.

After the caller is informed of the negative results, the system of the present invention advantageously offers counselling as at step 130. If the caller takes advantage of the counseling offered at step 130, the program shifts to step 132 whereat a professionally trained counsellor provides counselling information to the caller and encourages the caller to retest if there is any reason to believe that HIV antibodies will develop in the future. Otherwise, the program 84 shifts to step 133 whereat the computer system 84 terminated the call without revealing the caller's name thus providing confidentiality/anonymity for the person taking the test.

If the test results reported by the laboratory are positive, the computer program 84 shifts the program to step 134 whereat a counselor informs the caller of the test results. At step 134, the counselor further takes the opportunity to counsel the person being tested about how to get proper medical attention, face-to-face counseling and to determine if there are any people that the user should inform about the test results because they might also be infected with the HIV virus.

It should be noted that the principles of an anonymous/confidential testing procedure as disclosed herein can be used for other diseases where the user does not want his or her name disclosed. Furthermore, the procedure does not have to be limited to testing for diseases, but can be used in other fields.

From the foregoing, it will be observed that numerous modifications and variations can be effected without departing from the true spirit and scope of the novel concept of the present invention. It will be appreciated that the present disclosure is intended as an exemplification of the invention, and is not intended to limit the invention to the specific embodiment illustrated. The disclosure is intended to cover by the appended claims all such modifications as fall within the scope of the claims.

What is claimed is:

1. In a medical testing method wherein a user submits from a remote location a specimen to a testing facility to be tested for a medical condition, a method for processing a user communication prior to testing of said specimen, the method comprising the steps of:

querying said user as to whether said user desires counseling; and selectively routing said communication to a counselor if said user desires counseling.

2. A method according to claim 1, further comprising a step of establishing a file for said user upon receipt of said communication.

3. A method according to claim 2, said test result being selected from the group consisting of a positive result corresponding to the presence of a medical condition and a negative result corresponding to the absence of said medical condition.

4. A method according to claim 3, wherein said steps of querying and selectively routing said communication to a counselor are performed only if said test result is a negative result.

5. A method according to claim 3, wherein said medical condition is infection with HIV.

6. A method according to claim 1, further comprising the steps of:

receiving a specimen from said user;

testing said specimen and determining a test result;

receiving a subsequent communication from said user;

prior to accessing of said test result by said user, querying said user as to whether said user desires counseling; and selectively routing said subsequent communication to a counselor if said user desires counseling.

7. A method according to claim 6, wherein said specimen is an oral specimen.

8. A method according to claim 6, further comprising the step of:
routing said subsequent communication to a test result access call handler if said user does not desire counseling prior to receiving said test result;
providing said test result to said user;
querying said user as to whether said user desires counseling; and
selectively routing said subsequent communication to a counselor if said user desires counseling after receiving said test result.

9. A method according to claim 1, wherein said user is anonymously identified by a personal identification code.

10. A system for processing a user communication in connection with medical testing, said user submitting from a remote location a test specimen to a medical testing laboratory, the system comprising:
means for receiving a remote communication from a user;
means for querying said user as to whether said user desires counseling prior to submission of said specimen; and
means for selectively routing said communication to a counselor if said user desires counseling.

11. A system according to claim 10, further comprising means for establishing a file for said user upon receiving said communication.

12. A system according to claim 10, wherein said user is anonymously identified by a personal identification code.

13. A method for medical testing for a medical condition, comprising the steps of:
receiving a test specimen from a user;
testing said specimen and determining a test result;
receiving a remote communication from said user;
prior to accessing of said test result by said user, querying said user as to whether said user desires counseling;
selectively routing said communication to a counselor if said user desires counseling.

14. A method according to claim 13, wherein said specimen is an oral specimen.

15. A method according to claim 13, further comprising the steps of:
providing said test result to said user;
querying said user as to whether said user desires counseling; and
selectively routing said communication to a counselor if said user desires counseling after receiving said test result.

16. A method according to claim 13, wherein said user is anonymously identified by a personal identification code.

17. In a medical testing system wherein a user submits a specimen to a testing facility to be tested for a medical condition, a system comprising:
means for receiving a communication from a user subsequent to submission of said test specimen to the testing facility;
means for querying said user as to whether said user desires counseling prior to accessing a test result; and
means for selectively routing said communication to a counselor if said user desires counseling.

18. A system according to claim 17, wherein said user is anonymously identified by a personal identification code.

19. A medical testing method, comprising the steps of:
receiving a specimen from a user;
testing said specimen and determining a test result;
receiving a communication from said user;
providing said test result to said user;
querying said user as to whether said user desires counseling; and
selectively routing said communication to a counselor if said user desires counseling.

20. A method according to claim 19, wherein said specimen is an oral specimen.

21. A method according to claim 19, said test result being selected from the group consisting of a positive result corresponding to the presence of a medical condition and a negative result corresponding to the absence of said medical condition.

22. A method according to claim 21, wherein said steps of querying and selectively routing said communication to a counselor are performed only if said test result is a negative result.

23. A method according to claim 21, wherein said medical condition is infection with HIV.

24. A method according to claim 19, wherein said user is anonymously identified by a personal identification code.

25. In a medical testing system wherein a test specimen is received at a testing facility and is tested for a medical condition yielding a test result, a system comprising:
means for receiving a communication from said user;
means for providing said test result to said user;
means for querying said user as to whether said user desires counseling after said user has been provided with said result; and
means for selectively routing said communication to a counselor if said user desires counseling.

26. A system according to claim 25, said test result being selected from the group consisting of a positive result corresponding to the presence of a medical condition and a negative result corresponding to the absence of said medical condition.

27. A method according to claim 26, wherein said steps of querying and selectively routing said communication to a counselor are performed only if said test result is a negative result.

28. A system according to claim 26, wherein said medical condition is infection with HIV.

29. A system according to claim 25, wherein said user is anonymously identified by a personal identification code.

30. In a medical testing method wherein a user submits a specimen to a testing facility to be tested for a medical condition, a method for processing a user communication comprising:
receiving a communication from said user;
determining whether said user has previously established a user file; and
selectively routing said communication to a file generation call handler if said user has not previously established a user file.

31. A method according to claim 30, wherein said specimen is an oral specimen.

32. A method according to claim 30, wherein said user is anonymously identified by a personal identification code.

33. A method according to claim 30, including the steps of:
receiving a personal identification code;
verifying said personal identification code against a database of valid personal identification codes after receiving said personal identification code; and routing said user communication to said file generation call handler only if only if said personal identification code represents a valid personal identification code.

34. A method according to claim 30, wherein said user file includes a patient record and a call log, said patient record including non-identifying information about said user.

35. A method according to claim 34, wherein said non-identifying information includes the person's age.

36. A method according to claim 34, wherein said non-identifying information includes the person's gender.

37. A method according to claim 34, wherein said non-identifying information includes the person's ZIP code.

38. A method according to claim 34, wherein said non-identifying information includes the person's age and gender.

39. A method according to claim 34, wherein said non-identifying information includes the person's age, gender, and ZIP code.

40. A method according to claim 34, wherein said non-identifying information includes risk factors.

41. A method according to claim 34, wherein said non-identifying information includes the person's expected test results.

42. A method according to claim 30, further comprising the steps of:
   after generation of a user file by said file generation call handler, querying said user as to whether said user desires counseling; and
   routing said communication to a counselor if said user desires counseling.

43. A method according to claim 30, further comprising the steps of:
   querying said user as to whether said user desires counseling if said user has previously established a user file; and
   routing said communication to a counselor if said user desires counseling.

44. A method according to claim 43, further comprising the steps of:
   providing a test result to said user;
   querying said user as to whether said user desires counseling; and
   selectively routing said communication to a counselor if said user desires counseling after said user has been provided with said test result.

45. A method according to claim 44, said test result being selected from the group consisting of a positive result corresponding to the presence of a medical condition and a negative result corresponding to the absence of said medical condition.

46. A method according to claim 45, wherein said steps of querying and selectively routing said communication to a counselor are performed only if said test result is a negative result.

47. A method according to claim 45, wherein said medical condition is infection with HIV.

48. A method according to claim 30, including the step of authorizing the testing facility to perform a test on the specimen if said user has not previously established a user file.

49. A method according to claim 48, wherein said step of authorizing includes generating a laboratory order request.

50. A method according to claim 49, wherein said laboratory order request is anonymously identified by a personal code, said personal code being identified with said personal file.

51. A method for anonymous testing for a medical condition, comprising the steps of:
   receiving an oral specimen from a user;
   testing said oral specimen and obtaining a test result;
   receiving a communication from a user, said user being anonymously identified by a personal identification code; and
   providing said test result to said user.

52. A method according to claim 51, further comprising the steps of:
   prior to receiving said oral sample, providing an oral specimen collection kit to said user.

53. A method according to claim 52, wherein said personal identification code is unique to said kit.

54. A method according to claim 52, wherein said oral sample is a mucosal transudate sample.

55. A method according to claim 54, wherein said test specimen collection kit includes an absorbent pad for collection of said sample.

56. A method according to claim 51, wherein said medical condition is HIV.

57. A method for anonymous testing for a medical condition, comprising the steps of:
   obtaining an oral specimen collection kit, said kit being associated with a unique personal identification code;
   obtaining an oral specimen and associating said specimen with said kit;
   sending said oral specimen to a medical testing facility;
   initiating a communication with said testing facility;
   providing said personal identification code to said testing facility; and
   receiving a test result.

58. A method according to claim 57, wherein said oral sample is a mucosal transudate sample.

59. A method according to claim 58, wherein said test specimen collection kit includes an absorbent pad for collection of said sample.

60. A method according to claim 57, wherein said medical condition is HIV.

* * * * *